US012793821B2

(12) United States Patent
Rottkamp et al.

(10) Patent No.: US 12,793,821 B2
(45) **Date of Patent: *Nov. 10, 2026**

(54) METHODS AND SYSTEMS PROCESSING DATA

(71) Applicant: Cigna Intellectual Property, Inc., Wilmington, DE (US)

(72) Inventors: John Rottkamp, Canton, CT (US); Steven B. Miller, St. Louis, MO (US); Stacie Lukasiak, Franklin, TN (US); Jeffery P. Panter, Hixson, TN (US); William D. Harrington, Holland, PA (US)

(73) Assignee: Cigna Intellectual Property, Inc., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/243,072

(22) Filed: Jun. 19, 2025

(65) Prior Publication Data

US 2025/0316351 A1 Oct. 9, 2025

Related U.S. Application Data

(60) Continuation of application No. 18/127,969, filed on Mar. 29, 2023, now Pat. No. 12,347,535, which is a (Continued)

(51) Int. Cl.

| | |
|---|---|
| ***G16H 10/60*** | (2018.01) |
| ***G06F 16/21*** | (2019.01) |
| ***G06F 16/22*** | (2019.01) |
| ***G06F 16/2452*** | (2019.01) |
| ***G06F 16/248*** | (2019.01) |
| ***G06F 16/25*** | (2019.01) |

(Continued)

(52) U.S. Cl.
CPC ........... *G16H 10/60* (2018.01); *G06F 16/211* (2019.01); *G06F 16/221* (2019.01); *G06F 16/24522* (2019.01); *G06F 16/248* (2019.01); *G06F 16/258* (2019.01); *G06F 18/24155* (2023.01); *G06Q 40/08* (2013.01); *G16H 20/00* (2018.01)

(58) Field of Classification Search
CPC ........ G06Q 10/10; G06Q 40/08; G16H 20/00; G16H 20/10
See application file for complete search history.

(56) References Cited

U.S. PATENT DOCUMENTS

2014/0316796 A1* 10/2014 Cox ....................... G16H 20/10 705/2

* cited by examiner

*Primary Examiner* — Joseph D Burgess
(74) *Attorney, Agent, or Firm* — Miller Johnson

(57) ABSTRACT

Methods and systems for analyzing data are described. In one embodiment, a method comprises a processor receiving a data analysis algorithm over a network and executing the data analysis algorithm, the data analysis algorithm analyzing data stored in a database using machine learning to identify a database organizational format, the data analysis algorithm identifying one or more locations for a set of data stored on the database based on identifying the database organizational format, the data analysis algorithm parsing the set of data to identify whether any entries in the database associated with the set of data includes a particular value, and the data analysis algorithm communicating over the network at least a first number of entries in the database that include the particular value and a second number of entries in the database that do not include the particular value.

20 Claims, 8 Drawing Sheets

Related U.S. Application Data division of application No. 16/995,700, filed on Aug. 17, 2020, now Pat. No. 11,817,189.

(60) Provisional application No. 62/888,131, filed on Aug. 16, 2019.

(51) Int. Cl.

| | |
|---|---|
| ***G06F 18/2415*** | (2023.01) |
| ***G06Q 40/08*** | (2012.01) |
| ***G16H 20/00*** | (2018.01) |

METHODS AND SYSTEMS PROCESSING DATA

CROSS REFERENCE TO RELATED APPLICATIONS

The present disclosure is a continuation application and claims priority to U.S. patent application Ser. No. 18/127,969, filed on Mar. 29, 2023; said application Ser. No. 18/127,969 is a divisional application of and claims priority to U.S. patent application Ser. No. 16/995,700, titled "Methods and Systems for Processing Data", filed on Aug. 17, 2020 and issued as U.S. Pat. No. 11,817,189 on Nov. 14, 2023; said application Ser. No. 16/995,700 claims the benefit of provisional application 62/888,131 filed on Aug. 16, 2019. The entire disclosure of the above applications are herein incorporated by reference.

FIELD

The present disclosure relates generally to the technical field of data processing. In a specific example, the present disclosure may relate to processing medical data in a manner that is database format agnostic.

BACKGROUND

Conventional methods for processing and analyzing data stored in a database require an understanding of the database's organizational scheme or structure before performing any data analysis on the data stored in the database. That is, in order to process or analyze data stored in a database, a computer must first be aware of the database's organizational scheme or structure, such as by knowing which column of the database or which address(es) of the database stores the desired information to be analyzed. However, it would be advantageous to analyze data across numerous databases without prior knowledge of each database's organizational structure or without reformatting multiple databases for uniformity.

DETAILED DESCRIPTION

Figure 1:
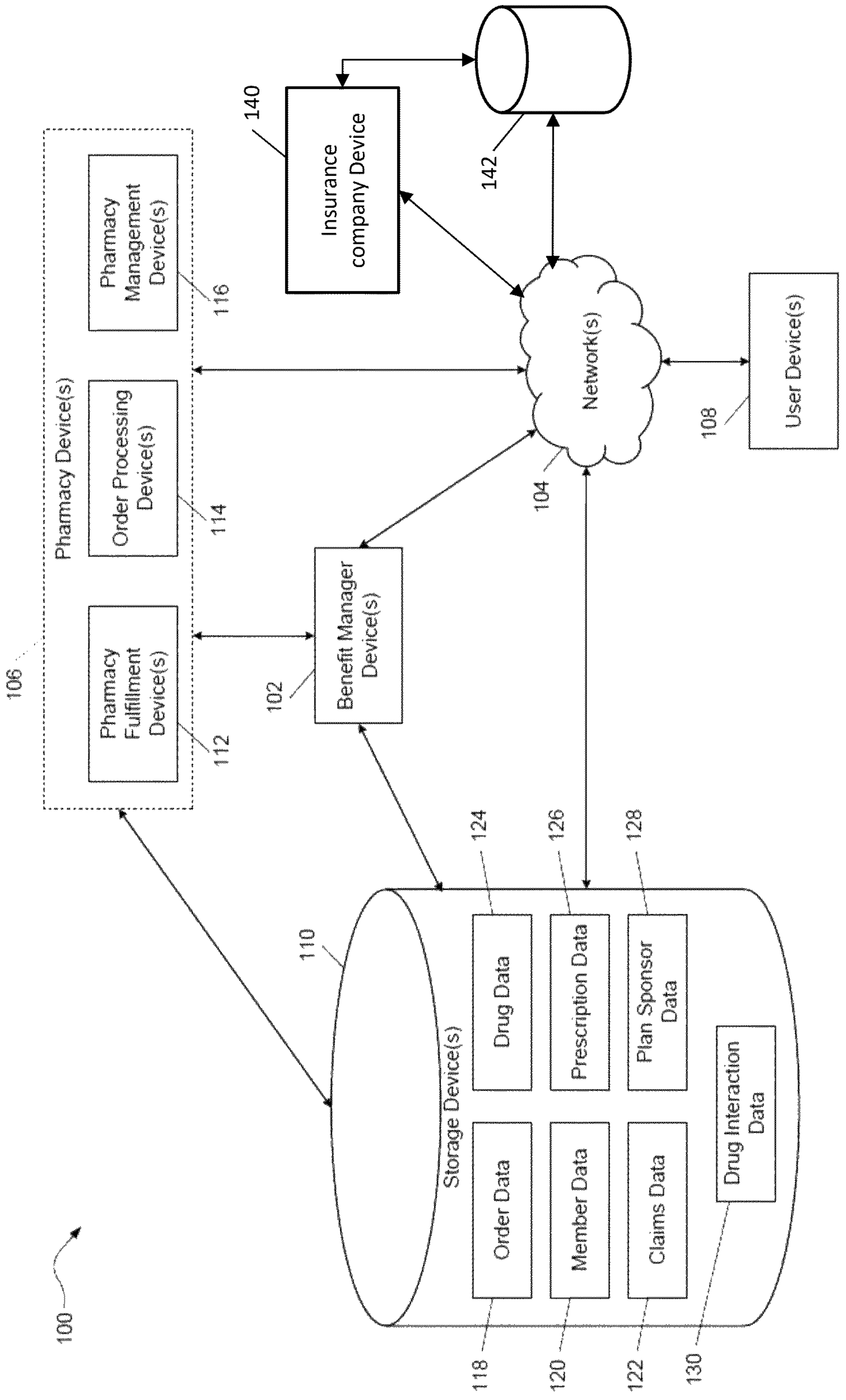
FIG. 1 is a functional block diagram of an example system including a high-volume pharmacy.

FIG. 1 is a block diagram of an example implementation of a system 100 for a high-volume pharmacy. While the system 100 is generally described as being deployed in a high-volume pharmacy or a fulfillment center (for example, a mail order pharmacy, a direct delivery pharmacy, etc.), the system 100 and/or components of the system 100 may otherwise be deployed (for example, in a lower-volume pharmacy, etc.). A high-volume pharmacy may be a pharmacy that is capable of filling at least some prescriptions mechanically. The system 100 may include a benefit manager device 102 and a pharmacy device 106 in communication with each other directly and/or over a network 104. The system 100 may also include a storage device 110.

The benefit manager device 102 is a device operated by an entity that is at least partially responsible for creation and/or management of the pharmacy or drug benefit. While the entity operating the benefit manager device 102 is typically a pharmacy benefit manager (PBM), other entities may operate the benefit manager device 102 on behalf of themselves or other entities (such as PBMs). For example, the benefit manager device 102 may be operated by a health plan, a retail pharmacy chain, a drug wholesaler, a data analytics or other type of software-related company, etc. In some implementations, a PBM that provides the pharmacy benefit may provide one or more additional benefits including a medical or health benefit, a rare genetic disease benefit, a dental benefit, a vision benefit, a wellness benefit, a radiology benefit, a pet care benefit, an insurance benefit, a long term care benefit, a nursing home benefit, etc. The PBM may, in addition to its PBM operations, operate one or more pharmacies. The pharmacies may be retail pharmacies, mail order pharmacies, etc.

Some of the operations of the PBM that operates the benefit manager device 102 may include the following activities and processes. A member (or a person on behalf of the member) of a pharmacy benefit plan may obtain a prescription drug at a retail pharmacy location (e.g., a location of a physical store) from a pharmacist or a pharmacist technician. The member may also obtain the prescription drug through mail order drug delivery from a mail order pharmacy location, such as the system 100. In some implementations, the member may obtain the prescription drug directly or indirectly through the use of a machine, such as a kiosk, a vending unit, a mobile electronic device 108, or a different type of mechanical device, electrical device, electronic communication device, and/or computing device. Such a machine may be filled with the prescription drug in prescription packaging, which may include multiple prescription components, by the system 100. The pharmacy benefit plan is administered by or through the benefit manager device 102.

The user device 108 may be a stand-alone device, or may be a multi-use device. Examples of the user device 108 include a set-top box (STB), a receiver card, a mobile telephone, a personal digital assistant (PDA), a display device, a portable gaming unit, and a computing system; however, other devices may also be used. For example, the user device 108 may include a mobile electronic device, such an IPHONE or IPAD device by Apple, Inc., mobile electronic devices powered by ANDROID by Google, Inc., and a BLACKBERRY device by Research In Motion Limited. The user device 108 also include other computing devices, such as desktop computing devices, notebook computing devices, netbook computing devices, gaming devices, and the like. Other types of electronic devices may also be used. Additionally or alternatively, the user device 108 can execute an application that may use a cellular phone function of the user device 108. The application may include instructions that when executed on the user device 108, in the benefit manager device 102, or pharmacy device 106, cause a machine to change its state or perform tasks within the machine and with other machines. Such devices become dedicated devices for executing the processes as described herein.

The member may have a copayment for the prescription drug that reflects an amount of money that the member is responsible to pay the pharmacy for the prescription drug. The money paid by the member to the pharmacy may come from, as examples, personal funds of the member, a health savings account (HSA) of the member or the member's family, a health reimbursement arrangement (HRA) of the member or the member's family, or a flexible spending account (FSA) of the member or the member's family. In some instances, an employer of the member may directly or indirectly fund or reimburse the member for the copayments.

The amount of the copayment required by the member may vary across different pharmacy benefit plans having different plan sponsors or clients and/or for different prescription drugs. The member's copayment may be a flat copayment (in one example, $10), coinsurance (in one example, 10%), and/or a deductible (for example, responsibility for the first $500 of annual prescription drug expense, etc.) for certain prescription drugs, certain types and/or classes of prescription drugs, and/or all prescription drugs. The copayment may be stored in the storage device 110 or determined by the benefit manager device 102.

In some instances, the member may not pay the copayment or may only pay a portion of the copayment for the prescription drug. For example, if a usual and customary cost for a generic version of a prescription drug is $4, and the member's flat copayment is $20 for the prescription drug, the member may only need to pay $4 to receive the prescription drug. In another example involving a worker's compensation claim, no copayment may be due by the member for the prescription drug.

In addition, copayments may also vary based on different delivery channels for the prescription drug. For example, the copayment for receiving the prescription drug from a mail order pharmacy location may be less than the copayment for receiving the prescription drug from a retail pharmacy location.

In conjunction with receiving a copayment (if any) from the member and dispensing the prescription drug to the member, the pharmacy submits a claim to the PBM for the prescription drug. After receiving the claim, the PBM (such as by using the benefit manager device 102) may perform certain adjudication operations including verifying eligibility for the member, identifying/reviewing an applicable formulary for the member to determine any appropriate copayment, coinsurance, and deductible for the prescription drug, and performing a drug utilization review (DUR) for the member. Further, the PBM may provide a response to the pharmacy (for example, the pharmacy system 100) following performance of at least some of the aforementioned operations.

As part of the adjudication, a plan sponsor (or the PBM on behalf of the plan sponsor) ultimately reimburses the pharmacy for filling the prescription drug when the prescription drug was successfully adjudicated. The aforementioned adjudication operations generally occur before the copayment is received and the prescription drug is dispensed. However in some instances, these operations may occur simultaneously, substantially simultaneously, or in a different order. In addition, more or fewer adjudication operations may be performed as at least part of the adjudication process.

The amount of reimbursement paid to the pharmacy by a plan sponsor and/or money paid by the member may be determined at least partially based on types of pharmacy networks in which the pharmacy is included. In some implementations, the amount may also be determined based on other factors. For example, if the member pays the pharmacy for the prescription drug without using the prescription or drug benefit provided by the PBM, the amount of money paid by the member may be higher than when the member uses the prescription or drug benefit. In some implementations, the amount of money received by the pharmacy for dispensing the prescription drug and for the prescription drug itself may be higher than when the member uses the prescription or drug benefit. Some or all of the foregoing operations may be performed by executing instructions stored in the benefit manager device 102 and/or an additional device.

Examples of the network 104 include a Global System for Mobile Communications (GSM) network, a code division multiple access (CDMA) network, 3rd Generation Partnership Project (3GPP), an Internet Protocol (IP) network, a Wireless Application Protocol (WAP) network, or an IEEE 802.11 standards network, as well as various combinations of the above networks. The network 104 may include an optical network. The network 104 may be a local area network or a global communication network, such as the Internet. In some implementations, the network 104 may include a network dedicated to prescription orders: a prescribing network such as the electronic prescribing network operated by Surescripts of Arlington, Virginia.

Moreover, although the system shows a single network 104, multiple networks can be used. The multiple networks may communicate in series and/or parallel with each other to link the devices 102-110.

The pharmacy device 106 may be a device associated with a retail pharmacy location (e.g., an exclusive pharmacy location, a grocery store with a retail pharmacy, or a general sales store with a retail pharmacy) or other type of pharmacy location at which a member attempts to obtain a prescription. The pharmacy may use the pharmacy device 106 to submit the claim to the PBM for adjudication.

Additionally, in some implementations, the pharmacy device 106 may enable information exchange between the pharmacy and the PBM. For example, this may allow the sharing of member information such as drug history that may allow the pharmacy to better service a member (for example, by providing more informed therapy consultation and drug interaction information). In some implementations, the benefit manager device 102 may track prescription drug fulfillment and/or other information for users that are not members, or have not identified themselves as members, at the time (or in conjunction with the time) in which they seek to have a prescription filled at a pharmacy.

The pharmacy device 106 may include a pharmacy fulfillment device 112, an order processing device 114, and a pharmacy management device 116 in communication with each other directly and/or over the network 104. The order processing device 114 may receive information regarding filling prescriptions and may direct an order component to one or more devices of the pharmacy fulfillment device 112 at a pharmacy. The pharmacy fulfillment device 112 may fulfill, dispense, aggregate, and/or pack the order components of the prescription drugs in accordance with one or more prescription orders directed by the order processing device 114.

In general, the order processing device 114 is a device located within or otherwise associated with the pharmacy to enable the pharmacy fulfilment device 112 to fulfill a prescription and dispense prescription drugs. In some implementations, the order processing device 114 may be an external order processing device separate from the pharmacy and in communication with other devices located within the pharmacy.

For example, the external order processing device may communicate with an internal pharmacy order processing device and/or other devices located within the system 100. In some implementations, the external order processing device may have limited functionality (e.g., as operated by a user requesting fulfillment of a prescription drug), while the internal pharmacy order processing device may have greater functionality (e.g., as operated by a pharmacist).

The order processing device 114 may track the prescription order as it is fulfilled by the pharmacy fulfillment device 112. The prescription order may include one or more prescription drugs to be filled by the pharmacy. The order processing device 114 may make pharmacy routing decisions and/or order consolidation decisions for the particular prescription order. The pharmacy routing decisions include what device(s) in the pharmacy are responsible for filling or otherwise handling certain portions of the prescription order. The order consolidation decisions include whether portions of one prescription order or multiple prescription orders should be shipped together for a user or a user family. The order processing device 114 may also track and/or schedule literature or paperwork associated with each prescription order or multiple prescription orders that are being shipped together. In some implementations, the order processing device 114 may operate in combination with the pharmacy management device 116.

The order processing device 114 may include circuitry, a processor, a memory to store data and instructions, and communication functionality. The order processing device 114 is dedicated to performing processes, methods, and/or instructions described in this application. Other types of electronic devices may also be used that are specifically configured to implement the processes, methods, and/or instructions described in further detail below.

In some implementations, at least some functionality of the order processing device 114 may be included in the pharmacy management device 116. The order processing device 114 may be in a client-server relationship with the pharmacy management device 116, in a peer-to-peer relationship with the pharmacy management device 116, or in a different type of relationship with the pharmacy management device 116. The order processing device 114 and/or the pharmacy management device 116 may communicate directly (for example, such as by using a local storage) and/or through the network 104 (such as by using a cloud storage configuration, software as a service, etc.) with the storage device 110.

The storage device 110 may include: non-transitory storage (for example, memory, hard disk, CD-ROM, etc.) in communication with the benefit manager device 102 and/or the pharmacy device 106 directly and/or over the network 104. The non-transitory storage may store order data 118, member data 120, claims data 122, drug data 124, prescription data 126, and/or plan sponsor data 128. Further, the system 100 may include additional devices, which may communicate with each other directly or over the network 104.

The order data 118 may be related to a prescription order. The order data may include type of the prescription drug (for example, drug name and strength) and quantity of the prescription drug. The order data 118 may also include data used for completion of the prescription, such as prescription materials. In general, prescription materials include an electronic copy of information regarding the prescription drug for inclusion with or otherwise in conjunction with the fulfilled prescription. The prescription materials may include electronic information regarding drug interaction warnings, recommended usage, possible side effects, expiration date, date of prescribing, etc. The order data 118 may be used by a high-volume fulfillment center to fulfill a pharmacy order.

In some implementations, the order data 118 includes verification information associated with fulfillment of the prescription in the pharmacy. For example, the order data 118 may include videos and/or images taken of (i) the prescription drug prior to dispensing, during dispensing, and/or after dispensing, (ii) the prescription container (for example, a prescription container and sealing lid, prescription packaging, etc.) used to contain the prescription drug prior to dispensing, during dispensing, and/or after dispensing, (iii) the packaging and/or packaging materials used to ship or otherwise deliver the prescription drug prior to dispensing, during dispensing, and/or after dispensing, and/or (iv) the fulfillment process within the pharmacy. Other types of verification information such as barcode data read from pallets, bins, trays, or carts used to transport prescriptions within the pharmacy may also be stored as order data 118.

The member data 120 includes information regarding the members associated with the PBM. The information stored as member data 120 may include personal information, personal health information, protected health information, etc. Examples of the member data 120 include name, address, telephone number, e-mail address, prescription drug history, etc. The member data 120 may include a plan sponsor identifier that identifies the plan sponsor associated with the member and/or a member identifier that identifies the member to the plan sponsor. The member data 120 may include a member identifier that identifies the plan sponsor associated with the user and/or a user identifier that identifies the user to the plan sponsor. The member data 120 may also include dispensation preferences such as type of label, type of cap, message preferences, language preferences, etc. In addition, the member data 112 can include or reference prescription numbers associated with the member. Such member data 112 may be protected data that cannot be accessed by third parties. Without such access, the member data 112 may not be pooled with third party data for analysis, thus restricting the pool of data and the accuracy of the analysis.

The member data 120 may be accessed by various devices in the pharmacy (for example, the high-volume fulfillment center, etc.) to obtain information used for fulfillment and shipping of prescription orders. In some implementations, an external order processing device operated by or on behalf of a member may have access to at least a portion of the member data 120 for review, verification, or other purposes.

In some implementations, the member data 120 may include information for persons who are users of the pharmacy but are not members in the pharmacy benefit plan being provided by the PBM. For example, these users may obtain drugs directly from the pharmacy, through a private label service offered by the pharmacy, the high-volume fulfillment center, or otherwise. In general, the use of the terms "member" and "user" may be used interchangeably.

The claims data 122 includes information regarding pharmacy claims adjudicated by the PBM under a drug benefit program provided by the PBM for one or more plan sponsors. In general, the claims data 122 includes an identification of the client that sponsors the drug benefit program under which the claim is made, and/or the member that purchased the prescription drug giving rise to the claim, the prescription drug that was filled by the pharmacy (e.g., the national drug code number, etc.), the dispensing date, generic indicator, generic product identifier (GPI) number, medication class, the cost of the prescription drug provided under the drug benefit program, the copayment/coinsurance amount, rebate information, and/or member eligibility, etc. Additional information may be included.

In some implementations, other types of claims beyond prescription drug claims may be stored in the claims data 122. For example, medical claims, dental claims, wellness claims, or other types of health-care-related claims for members may be stored as a portion of the claims data 122.

In some implementations, the claims data 122 includes claims that identify the members with whom the claims are associated. Additionally or alternatively, the claims data 122 may include claims that have been de-identified (that is, associated with a unique identifier but not with a particular, identifiable member).

The drug data 124 may include drug name (e.g., technical name and/or common name), other names by which the drug is known, active ingredients, an image of the drug (such as in pill form), typical dosing instructions, etc. The drug data 124 may include information associated with a single medication or multiple medications. However, dosing instructions may come from the claims data 122 if the doctor prescribed dosing instructions different from the typical dosing instructions.

The prescription data 126 may include information regarding prescriptions that may be issued by prescribers on behalf of users, who may be members of the pharmacy benefit plan—for example, to be filled by a pharmacy. Examples of the prescription data 126 include user names, medication or treatment (such as lab tests), dosing information, etc. The prescriptions may include electronic prescriptions or paper prescriptions that have been scanned. In some implementations, the dosing information reflects a frequency of use (e.g., once a day, twice a day, before each meal, etc.) and a duration of use (e.g., a few days, a week, a few weeks, a month, etc.).

Furthermore, the drug interaction data 130 can include all known interactions between various prescription drugs. The known interactions can be negative, positive, or benign. Further still, the drug interaction data 130 can include known interactions between each prescription drug and over-the-counter drugs, known interactions between each prescription drug and vitamins or medical herbs (e.g. St. John's Wort), or known interactions between each prescription drug and commonly used substances, such as alcohol.

In some implementations, the order data 118 may be linked to associated member data 120, claims data 122, drug data 124, and/or prescription data 126.

The plan sponsor data 128 includes information regarding the plan sponsors of the PBM. Examples of the plan sponsor data 128 include company name, company address, contact name, contact telephone number, contact e-mail address, etc.

In addition, the benefit manager device 102 may communicate with one or more insurance company device(s) 140 over the network 104. Additionally, each insurance company device 140 can communicate with the pharmacy device 106 and with the user device(s) 108 over the network 104. Each of the one or more insurance company devices 140 can be associated with a respective insurance company, which may be the same or a different entity than the PBM entity operating the benefit manager device 102. For example, the insurance company may offer insurance coverage to insured members, insured clients, or insured patients affiliated with the insurance company. As used herein, "insured members", "insured patients", and "insured clients" are members, patients, or clients of the insurance company. In some implementations, the insurance company may provide one or more benefits including a medical or health benefit, a rare genetic disease benefit, a dental benefit, a vision benefit, a wellness benefit, a radiology benefit, a pet care benefit, an insurance benefit, a long term care benefit, a nursing home benefit, etc. In addition, the insurance company may offer the pharmacy or drug benefit offered by the PBM to the insured members, insured clients, or insured patients as part of an insurance policy. Further still, the insurance company may automatically offer and enroll PBM clients and members, who qualify, in a benefit (e.g. the rare genetic disease benefit) offered by the insurance company. Alternatively, the rare gene disease benefit can be offered by the PBM. While the rare gene disease benefit (i.e. rare gene insurance product) is described as the benefit provided, the exemplary embodiments are not limited to a rare gene disease benefit, and auto-enrollment of other insurance products is contemplated.

The insurance company device 140 may reference data from an associated insurance storage device 142 in making insurance decisions, such as repayment of insurance claims or enrolling insured members or insured patients into an insurance benefit plan (e.g. the rare genetic disease benefit product). The insurance storage device 142 may include: non-transitory storage (for example, memory, hard disk, CD-ROM, etc.) in communication with the insurance company device 140 directly and/or over the network 104. The insurance storage device 142 may store data similar to the storage device 110 for insurance purposes. For example, the insurance storage device 142 can store insured member data, insured claims data, insured drug data, and insured prescription data, etc. The insured data stored by the insurance storage device 142 may be similar to the data stored in the storage device 110, but the insured data may reflect business differences between the insurance company and the PBM. For example, the insured claims data may reflect prescription drug payment claims and further include claims for the payment of medical services or other medical procedures, such as surgeries, diagnostic scans, or medical testing. In some embodiments, the insured claims data or the insured member data can include ICD10 codes and national drug codes (NDC).

The data stored in the insurance storage device 142 may have a unique database organizational format or structure, which may be the same or different from a database organizational format or structure used by the storage device 110. For example, the database organizational format or structure used by the insurance storage device 142 may be unknown to the benefit manager device 102 or proprietary to the insurance company. The database organizational format or structure can include column numbers or addresses for specific data, such as, for example, a claims data column or a drug data column used to organize the data stored in the insurance storage device 142. In a database having columns, the rows can be associated with insured members. Also, the data stored in a first insurance storage device 142 may have a unique or different database organizational format or structure from a second insurance storage device 142.

Furthermore, the insurance company device 140 may receive a data analysis algorithm from the benefit manager device 102, and the insurance company device 140 may execute the data analysis algorithm. By executing the data analysis algorithm, the insurance company device 140 can analyze data stored in the insurance storage device 142 to make a determination regarding each insured member or each insured patient (e.g. whether to enroll each insured member or each insured patient in a rage genetic disease benefit). In some embodiments, the determination can simply be a yes or no flag for all or subsets of its insured members or insured clients. For example, the determination can indicate whether all or a subset of the insured members, insured clients, or insured patients are eligible for a rare gene disease benefit. In some embodiments, the subsets of data can correspond to all insured members or insured patients associated with an insured client, such as a company offering a healthcare insurance benefit to employees of the company. For example, the company can include 50 employees, and the data analysis algorithm can determine whether each of the 50 employees is eligible for the rare gene disease benefit. In some embodiments, a finding that one employee is ineligible results in ineligibility for all employees. Alternatively, a finding that one employee is ineligible results in only that employee being ineligible for the insurance benefit.

After executing the data analysis algorithm, the insurance company device 140 can communicate the determination to the benefit manager device 102. In some embodiments, the determination may not return insured client, insured member, or insured patient names, medical information, or private information, but instead, the determination can only return a yes or no value (e.g. 1 or 0 value) for all or the subset of the data analyzed by the data analysis algorithm to the benefit manager device 102. In this manner, no private data is shared between the benefit manager device 102 and the insurance company device 140.

Figure 2:
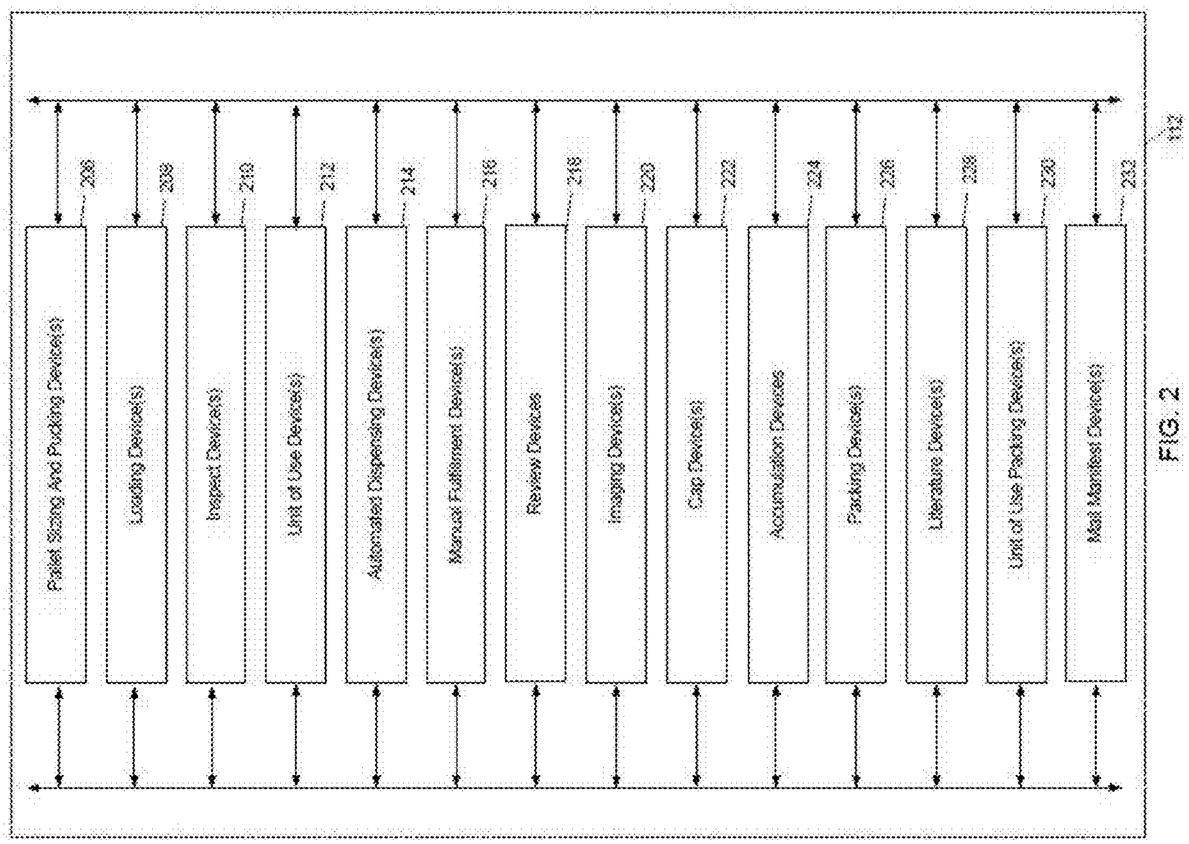
FIG. 2 is a functional block diagram of an example pharmacy fulfillment device, which may be deployed within the system of FIG. 1.

FIG. 2 illustrates the pharmacy fulfillment device 112 according to an example implementation. The pharmacy fulfillment device 112 may be used to process and fulfill prescriptions and prescription orders. After fulfillment, the fulfilled prescriptions are packed for shipping.

The pharmacy fulfillment device 112 may include devices in communication with the benefit manager device 102, the order processing device 114, and/or the storage device 110, directly or over the network 104. Specifically, the pharmacy fulfillment device 112 may include pallet sizing and pucking device(s) 206, loading device(s) 208, inspect device(s) 210, unit of use device(s) 212, automated dispensing device(s) 214, manual fulfillment device(s) 216, review devices 218, imaging device(s) 220, cap device(s) 222, accumulation devices 224, packing device(s) 226, literature device(s) 228, unit of use packing device(s) 230, and mail manifest device(s) 232. Further, the pharmacy fulfillment device 112 may include additional devices, which may communicate with each other directly or over the network 104.

In some implementations, operations performed by one of these devices 206-232 may be performed sequentially, or in parallel with the operations of another device as may be coordinated by the order processing device 114. In some implementations, the order processing device 114 tracks a prescription with the pharmacy based on operations performed by one or more of the devices 206-232.

In some implementations, the pharmacy fulfillment device 112 may transport prescription drug containers, for example, among the devices 206-232 in the high-volume fulfillment center, by use of pallets. The pallet sizing and pucking device 206 may configure pucks in a pallet. A pallet may be a transport structure for a number of prescription containers, and may include a number of cavities. A puck may be placed in one or more than one of the cavities in a pallet by the pallet sizing and pucking device 206. The puck may include a receptacle sized and shaped to receive a prescription container. Such containers may be supported by the pucks during carriage in the pallet. Different pucks may have differently sized and shaped receptacles to accommodate containers of differing sizes, as may be appropriate for different prescriptions.

The arrangement of pucks in a pallet may be determined by the order processing device 114 based on prescriptions that the order processing device 114 decides to launch. The arrangement logic may be implemented directly in the pallet sizing and pucking device 206. Once a prescription is set to be launched, a puck suitable for the appropriate size of container for that prescription may be positioned in a pallet by a robotic arm or pickers. The pallet sizing and pucking device 206 may launch a pallet once pucks have been configured in the pallet.

The loading device 208 may load prescription containers into the pucks on a pallet by a robotic arm, a pick and place mechanism (also referred to as pickers), etc. In various implementations, the loading device 208 has robotic arms or pickers to grasp a prescription container and move it to and from a pallet or a puck. The loading device 208 may also print a label that is appropriate for a container that is to be loaded onto the pallet, and apply the label to the container. The pallet may be located on a conveyor assembly during these operations (e.g., at the high-volume fulfillment center, etc.).

The inspect device 210 may verify that containers in a pallet are correctly labeled and in the correct spot on the pallet. The inspect device 210 may scan the label on one or more containers on the pallet. Labels of containers may be scanned or imaged in full or in part by the inspect device 210. Such imaging may occur after the container has been lifted out of its puck by a robotic arm, picker, etc., or may be otherwise scanned or imaged while retained in the puck. In some implementations, images and/or video captured by the inspect device 210 may be stored in the storage device 110 as order data 118.

The unit of use device 212 may temporarily store, monitor, label, and/or dispense unit of use products. In general, unit of use products are prescription drug products that may be delivered to a user or member without being repackaged at the pharmacy. These products may include pills in a container, pills in a blister pack, inhalers, etc. Prescription drug products dispensed by the unit of use device 212 may be packaged individually or collectively for shipping, or may be shipped in combination with other prescription drugs dispensed by other devices in the high-volume fulfillment center.

At least some of the operations of the devices 206-232 may be directed by the order processing device 114. For example, the manual fulfillment device 216, the review device 218, the automated dispensing device 214, and/or the packing device 226, etc. may receive instructions provided by the order processing device 114.

The automated dispensing device 214 may include one or more devices that dispense prescription drugs or pharmaceuticals into prescription containers in accordance with one or multiple prescription orders. In general, the automated dispensing device 214 may include mechanical and electronic components with, in some implementations, software and/or logic to facilitate pharmaceutical dispensing that would otherwise be performed in a manual fashion by a pharmacist and/or pharmacist technician. For example, the automated dispensing device 214 may include high-volume fillers that fill a number of prescription drug types at a rapid rate and blister pack machines that dispense and pack drugs into a blister pack. Prescription drugs dispensed by the automated dispensing devices 214 may be packaged individually or collectively for shipping, or may be shipped in combination with other prescription drugs dispensed by other devices in the high-volume fulfillment center.

The manual fulfillment device 216 controls how prescriptions are manually fulfilled. For example, the manual fulfillment device 216 may receive or obtain a container and enable fulfillment of the container by a pharmacist or pharmacy technician. In some implementations, the manual fulfillment device 216 provides the filled container to another device in the pharmacy fulfillment devices 112 to be joined with other containers in a prescription order for a user or member.

In general, manual fulfillment may include operations at least partially performed by a pharmacist or a pharmacy technician. For example, a person may retrieve a supply of the prescribed drug, may make an observation, may count out a prescribed quantity of drugs and place them into a prescription container, etc. Some portions of the manual fulfillment process may be automated by use of a machine. For example, counting of capsules, tablets, or pills may be at least partially automated (such as through use of a pill counter). Prescription drugs dispensed by the manual fulfillment device 216 may be packaged individually or collectively for shipping, or may be shipped in combination with other prescription drugs dispensed by other devices in the high-volume fulfillment center.

The review device 218 may process prescription containers to be reviewed by a pharmacist for proper pill count, exception handling, prescription verification, etc. Fulfilled prescriptions may be manually reviewed and/or verified by a pharmacist, as may be required by state or local law. A pharmacist or other licensed pharmacy person who may dispense certain drugs in compliance with local and/or other laws may operate the review device 218 and visually inspect a prescription container that has been filled with a prescription drug. The pharmacist may review, verify, and/or evaluate drug quantity, drug strength, and/or drug interaction concerns, or otherwise perform pharmacist services. The pharmacist may also handle containers which have been flagged as an exception, such as containers with unreadable labels, containers for which the associated prescription order has been canceled, containers with defects, etc. In an example, the manual review can be performed at a manual review station.

The imaging device 220 may image containers once they have been filled with pharmaceuticals. The imaging device 220 may measure a fill height of the pharmaceuticals in the container based on the obtained image to determine if the container is filled to the correct height given the type of pharmaceutical and the number of pills in the prescription. Images of the pills in the container may also be obtained to detect the size of the pills themselves and markings thereon. The images may be transmitted to the order processing device 114 and/or stored in the storage device 110 as part of the order data 118.

The cap device 222 may be used to cap or otherwise seal a prescription container. In some implementations, the cap device 222 may secure a prescription container with a type of cap in accordance with a user preference (e.g., a preference regarding child resistance, etc.), a plan sponsor preference, a prescriber preference, etc. The cap device 222 may also etch a message into the cap, although this process may be performed by a subsequent device in the high-volume fulfillment center.

The accumulation device 224 accumulates various containers of prescription drugs in a prescription order. The accumulation device 224 may accumulate prescription containers from various devices or areas of the pharmacy. For example, the accumulation device 224 may accumulate prescription containers from the unit of use device 212, the automated dispensing device 214, the manual fulfillment device 216, and the review device 218. The accumulation device 224 may be used to group the prescription containers prior to shipment to the member.

The literature device 228 prints, or otherwise generates, literature to include with each prescription drug order. The literature may be printed on multiple sheets of substrates, such as paper, coated paper, printable polymers, or combinations of the above substrates. The literature printed by the literature device 228 may include information required to accompany the prescription drugs included in a prescription order, other information related to prescription drugs in the order, financial information associated with the order (for example, an invoice or an account statement), etc.

In some implementations, the literature device 228 folds or otherwise prepares the literature for inclusion with a prescription drug order (e.g., in a shipping container). In other implementations, the literature device 228 prints the literature and is separate from another device that prepares the printed literature for inclusion with a prescription order.

The packing device 226 packages the prescription order in preparation for shipping the order. The packing device 226 may box, bag, or otherwise package the fulfilled prescription order for delivery. The packing device 226 may further place inserts (e.g., literature or other papers, etc.) into the packaging received from the literature device 228. For example, bulk prescription orders may be shipped in a box, while other prescription orders may be shipped in a bag, which may be a wrap seal bag.

The packing device 226 may label the box or bag with an address and a recipient's name. The label may be printed and affixed to the bag or box, be printed directly onto the bag or box, or otherwise associated with the bag or box. The packing device 226 may sort the box or bag for mailing in an efficient manner (e.g., sort by delivery address, etc.). The packing device 226 may include ice or temperature sensitive elements for prescriptions that are to be kept within a temperature range during shipping (for example, this may be necessary in order to retain efficacy). The ultimate package may then be shipped through postal mail, through a mail order delivery service that ships via ground and/or air (e.g., UPS, FEDEX, or DHL, etc.), through a delivery service, through a locker box at a shipping site (e.g., AMAZON locker or a PO Box, etc.), or otherwise.

The unit of use packing device 230 packages a unit of use prescription order in preparation for shipping the order. The unit of use packing device 230 may include manual scanning of containers to be bagged for shipping to verify each container in the order. In an example implementation, the manual scanning may be performed at a manual scanning station. The pharmacy fulfillment device 112 may also include a mail manifest device 232 to print mailing labels used by the packing device 226 and may print shipping manifests and packing lists.

While the pharmacy fulfillment device 112 in FIG. 2 is shown to include single devices 206-232, multiple devices may be used. When multiple devices are present, the multiple devices may be of the same device type or models, or may be a different device type or model. The types of devices 206-232 shown in FIG. 2 are example devices. In other configurations of the system 100, lesser, additional, or different types of devices may be included.

Moreover, multiple devices may share processing and/or memory resources. The devices 206-232 may be located in the same area or in different locations. For example, the devices 206-232 may be located in a building or set of adjoining buildings. The devices 206-232 may be interconnected (such as by conveyors), networked, and/or otherwise in contact with one another or integrated with one another (e.g., at the high-volume fulfillment center, etc.). In addition, the functionality of a device may be split among a number of discrete devices and/or combined with other devices.

The operation of the devices in FIG. 2 may be dependent on the pooling of data from different database sources (e.g., different insurance companies) for analysis. However, such data may not be pooled due to technical regulations, legal regulations or for other reasons. In an example embodiment, the tool or engine for analyzing the data can be shared. The tool can analyze the data and provide an indication of whether each member record or an individual member record in the respective database in the pool of databases is flagged as in the covered group.

Figure 3:
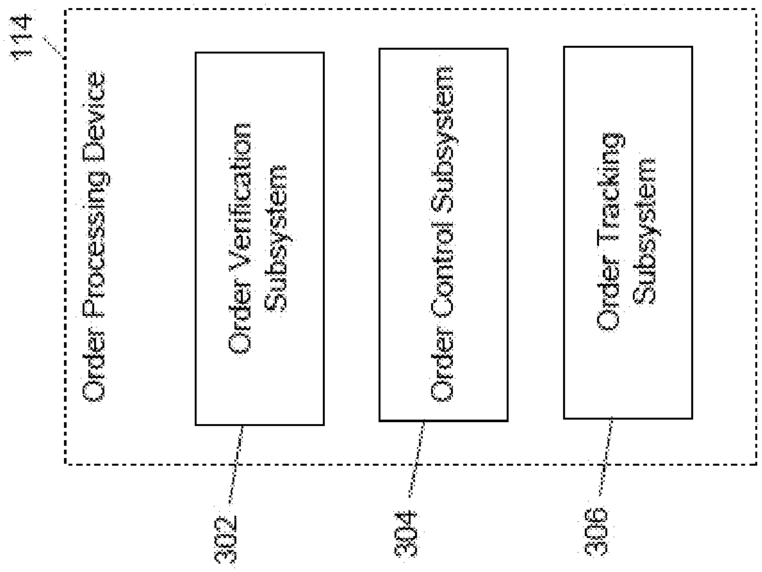
FIG. 3 is a functional block diagram of an example order processing device, which may be deployed within the system of FIG. 1.

FIG. 3 illustrates the order processing device 114 according to an example implementation. The order processing device 114 may be used by one or more operators to generate prescription orders, make routing decisions, make prescription order consolidation decisions, track literature with the system 100, and/or view order status and other order related information. For example, the prescription order may be comprised of order components.

The order processing device 114 may receive instructions to fulfill an order without operator intervention. An order component may include a prescription drug fulfilled by use of a container through the system 100. The order processing device 114 may include an order verification subsystem 302, an order control subsystem 304, and/or an order tracking subsystem 306. Other subsystems may also be included in the order processing device 114.

The order verification subsystem 302 may communicate with the benefit manager device 102 to verify the eligibility of the member and review the formulary to determine appropriate copayment, coinsurance, and deductible for the prescription drug and/or perform a DUR (drug utilization review). Other communications between the order verification subsystem 302 and the benefit manager device 102 may be performed for a variety of purposes.

The order control subsystem 304 controls various movements of the containers and/or pallets along with various filling functions during their progression through the system 100. In some implementations, the order control subsystem 304 may identify the prescribed drug in one or more than one prescription orders as capable of being fulfilled by the automated dispensing device 214. The order control subsystem 304 may determine which prescriptions are to be launched and may determine that a pallet of automated-fill containers is to be launched.

The order control subsystem 304 may determine that an automated-fill prescription of a specific pharmaceutical is to be launched and may examine a queue of orders awaiting fulfillment for other prescription orders, which will be filled with the same pharmaceutical. The order control subsystem 304 may then launch orders with similar automated-fill pharmaceutical needs together in a pallet to the automated dispensing device 214. As the devices 206-232 may be interconnected by a system of conveyors or other container movement systems, the order control subsystem 304 may control various conveyors: for example, to deliver the pallet from the loading device 208 to the manual fulfillment device 216 from the literature device 228, paperwork as needed to fill the prescription.

The order tracking subsystem 306 may track a prescription order during its progress toward fulfillment. The order tracking subsystem 306 may track, record, and/or update order history, order status, etc. The order tracking subsystem 306 may store data locally (for example, in a memory) or as a portion of the order data 118 stored in the storage device 110.

Example methods and systems for analyzing data across databases are described. In the following description, for purposes of explanation, numerous specific details are set forth in order to provide a thorough understanding of example embodiments. It will be evident, however, to one of ordinary skill in the art that embodiments of the present disclosure may be practiced without these specific details.

Significant advancements have been made in the medical field of gene therapy treatments. Some gene therapy treatments include pharmaceutical drugs, which are notable for being curative drugs. However, these gene therapy pharmaceuticals are also known for being extremely expensive to purchase. For example, Zolgensma, which can cure spinal muscular atrophy, can cost $2.1 million, and Luxterna, which can cure a specific form of blindness (Leber's congenital amaurosis), can cost up to $800,000. In many cases, conventional insurance companies do not cover the pharmaceutical costs associated with these gene therapy drugs. As such, these curative pharmaceuticals are unaffordable to the average consumer. Other gene therapy drugs exist for other diseases as well, such as Roctavian, which treats hemophilia, and others.

To offset the extreme pharmaceutical costs associated with these special and expensive drugs, a rare gene disease insurance product is envisioned. However, it is understood that delivering the rare gene disease insurance product at a low cost (e.g. $1/month) will require significant enrollment by many insured clients and insured members, including numerous insured members who do not have the rare genetic disease, to offset the risk of insuring the small number of insured members who do have the rare genetic disease. Indeed, one insurance company (e.g. Cigna Corp.) alone or one insurance company division (e.g. Cigna Health Care of Illinois, Inc.) may not have enough eligible members to underwrite a rare genetic disease insurance benefit offered at a low cost, and the rare disease insurance product may need to be offered to insured clients and insured members of multiple insurance companies or multiple insurance company divisions for this low cost to be achieved. Even though the existence of these rare diseases is very low, the extreme cost of the curative pharmaceuticals will still require significant pooling of insured clients and insured members (e.g. millions of insured members paying $1/month) for underwriting to approve an insurance benefit offered at this low cost. The disclosed embodiments described herein can assist in the pooling process to identify potential candidates across multiple insurance companies or multiple insurance company divisions by analyzing data across multiple databases associated with multiple insurance companies or multiple insurance company divisions. This is one example of how to pool databases together for analysis when the underlying data in the individual databases are not able to be combined for analysis.

Figure 4:
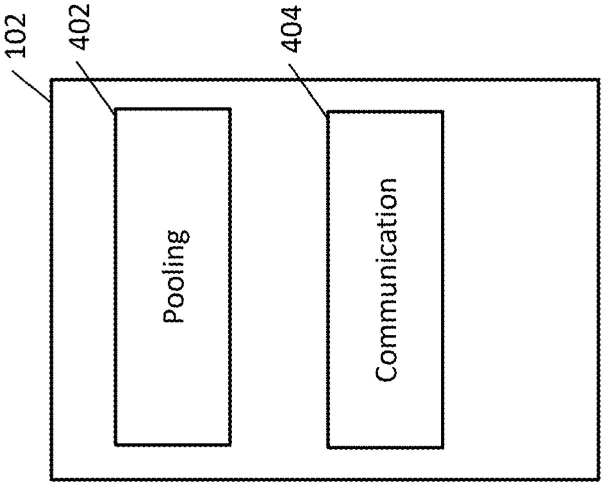
FIG. 4 is a block diagram of an example benefit manager device that may be deployed within the system of FIG. 1, according to an example embodiment.

FIG. 4 illustrates the benefit manager device 102, according to an example embodiment. The benefit manager device 102 may be deployed in the system 100 or may otherwise be used.

The benefit manager device 102 may include a pooling subsystem 402. In some embodiments, the pooling subsystem 402 may define the criterion that identifies whether or not a member, an insured member, a group of members associated with a client, or a group of insured members associated with an insured client are eligible for the rare gene insurance product. In some embodiments, the pooling subsystem 402 can include artificial intelligence or machine learning (e.g. linear discriminant analysis, maximum entropy classifiers, logistic regression, Naïve Bayes classifiers, neural networks, or other patter recognizing algorithms) that can analyze a database, recognize organization patterns, and identifies the database's organizational format or structure. Upon knowing the database's organizational format or structure, a data analysis algorithm of the pooling subsystem 402 can analyze data associated with a particular column or address of the database to identify whether or not one or all of the insured members are eligible for the rare gene insurance product.

The benefit manager device 102 may also include a communication subsystem 404. In some embodiments, the benefit manager device 102 may implement the communication subsystem 404 to communicate with the insurance company device 140. In some embodiments, the benefit manager device 102 can share the data analysis algorithm with the insurance company device 140 using the communication subsystem 404. In some embodiments, sharing the data analysis algorithm can include the communication module 404 uploading the data analysis algorithm to the insurance company device 140. After receiving the data analysis algorithm, the insurance company device 140 can execute the data analysis algorithm on the data stored in the insurance storage device 142 to identify if some, all, or none of the insured members associated with the insurance company qualify for the rare gene insurance product. Furthermore, the communication subsystem 404 can receive a determination of whether some, all, or none of the insured members of the insurance company qualify for the rare gene insurance product. In some embodiments, the communications subsystem 404 can receive the names of the insured members who qualified for the rare gene insurance policy, the communications subsystem 404 can pass the names of the insured members to the pooling subsystem 402, and the pooling subsystem 402 can automatically enroll the eligible insured members to the rare gene insurance product. In another embodiment, the communication subsystem 404 can receive only numbers of enrolled insured members and premium payments of those enrolled insured members. In the second embodiment, the insurance company may automatically enroll the eligible members, add the enrollment cost (e.g. $1/month) to each member's insurance premium, and repay the PBM anytime an eligible member submits a claim for a rare genetic disease drug therapy. In another embodiment, the insurance company device 140 may request confirmation from an insured client that they want to enroll all eligible members in the rare genetic disease insurance product.

Figure 5:
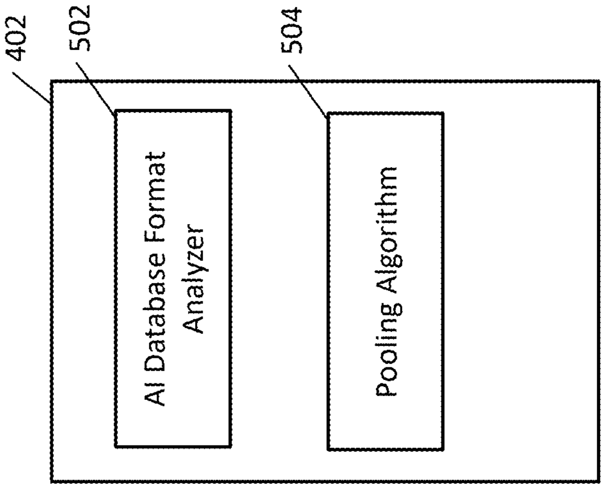
FIG. 5 is a block diagram of an example pooling subsystem that may be deployed within the benefit manager device of FIG. 4, according to an example embodiment.

FIG. 5 illustrates an example pooling subsystem 404 that may be deployed in the benefit manager device 102 or otherwise deployed in another system. One or more modules are communicatively coupled and included in the pooling subsystem 404 to enable the sharing of the data analysis algorithm with other entities and also executing the data analysis algorithm on any database regardless of the database's organizational structure and without previous knowledge of the database's organizational structure. The modules of the pooling subsystem 404 may include an artificial intelligence module 502 and a data analysis algorithm module 504. Other modules may also be included.

The artificial intelligence module 502 may include machine learning algorithms that sort through data in a database (e.g. the insurance storage device 142) to identify the database's organizational structure. For example, the database's organizational structure may store data in columns or according to another organizational schema. For examples, the columns of the database can include ICD10 codes, NCD codes, and other data representing an insured member's medical history. The artificial intelligence module 502 can analyze some or all of the data in the database to identify how the database has been organized and where relevant data is located. The artificial intelligence module 502 may train based on common database organizational structures, such as SQL database structures, relational databases, column-oriented databases, operational databases, key-value databases, MySQL, DB2, Microsoft SQL Server, NoSQL, etc. For example, typically, databases include data values indicating how the data has been organized, and the artificial intelligence algorithm can search for that indicating data. Furthermore, the artificial intelligence module 502 can search for ICD10 codes and NCD codes (or other medical diagnosis or treatment codes) to find where the claims data, diagnosis history, or prescription drug history is stored for each insured member or member (e.g. determine which database column stores the insured claim data). Once the artificial intelligence module 502 identifies the database organizational structure and the locations where the relevant data (e.g. claims data, ICD10 codes, NCD codes) is located, the artificial intelligence module 502 can report the location of the relevant data to the data analysis algorithm module 504.

In some embodiments, the artificial intelligence module 502 can be omitted, and the insurance company's IT department or other user can provide the necessary database column values or address values to be searched to the data analysis algorithm. In this embodiment, the insurance company IT department can make the necessary changes to the data analysis algorithm.

The data analysis algorithm module 504 may define the algorithm that determines whether each insured member of an insurance company or a member of the PBM is eligible for the rare gene insurance product. The method steps of the data analysis algorithm module 504 are illustrated with reference to FIG. 6. The data analysis algorithm module 504 can receive the database locations for relevant data, such as claims data including diagnosis history or prescription drug history for each member, from either the artificial intelligence module 502 or the insurance company IT department, and the data analysis algorithm module 504 can search for a particular disease diagnosis or a particular drug prescribed in the claims data to identify whether the patient is eligible for the rare gene insurance product. In some embodiments, the data analysis algorithm module 504 may also or alternatively consider a patient's birth date or employment date in determining eligibility.

Figure 6:
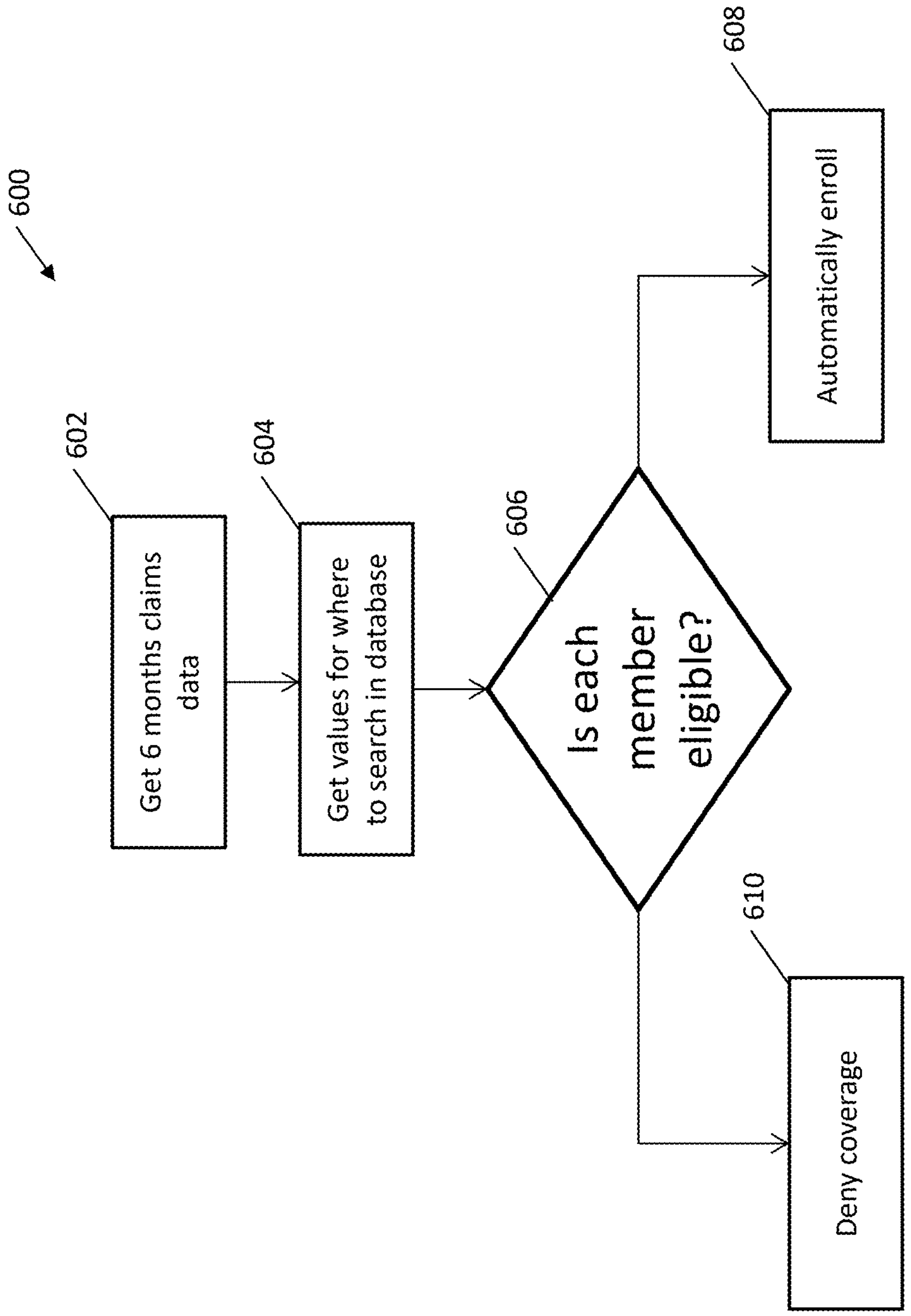
FIG. 6 is a block diagram of a flowchart illustrating methods for pooling clients into a rare gene therapy insurance product, according to an example embodiment.

FIG. 6 illustrates a method 600 for determining whether an individual data record can be flagged as with a computed subset with first combining the multiple databases for analysis. An insured member (member record) is eligible for a rare gene insurance policy according to an example embodiment. The method 600 may be performed by the insurance company device 140 after receiving the data analysis algorithm from the benefit manager device 102, by the benefit manager device 102, partially by the benefit manager device 102 and partially by the insurance company device 140, or may be otherwise performed. For the sake of simplicity, the insurance company device 140 will be described as performing the steps of the method 600, but the embodiments described herein are not so limited.

According to an exemplary embodiment, the insurance company device 140 executing the data analysis algorithm can receive insured claims data from the insurance storage device 142, which may be a database, in step 602. According to an exemplary embodiment, the insurance company device 140 executing the data analysis algorithm can receive claims data from a predetermined period of time, such as the most recent six months. Alternatively, the insurance company device 140 executing the data analysis algorithm can receive all claims data stored in the database regardless of timeframe. Subsequently, the insurance company device 140 executing the data analysis algorithm can receive a database location (e.g. a column number or addresses) where diagnosis codes and prescription drug codes (e.g. ICD10 and NCD codes) are stored in step 604. Alternatively, the insurance company device 140 executing the data analysis algorithm can receive a database location (e.g. a column number or addresses) where insured member birthdates or insured member employment start dates are stored. In some embodiments, the insurance company device 140 executing the data analysis algorithm can receive this database location from the artificial intelligence module 502 or as an input from a user, as described in detail above.

Subsequently, the insurance company device 140 executing the data analysis algorithm can parse database entries to identify whether each insured member is eligible for the rare gene insurance product in step 606. In some embodiments, the insurance company device 140 executing the data analysis algorithm can identify whether each insured member is eligible for the rare gene insurance product by determining whether each member is associated with a specific ICD10 code or a specific NCD code (or other medical treatment or diagnosis code). By finding a specific medical code, the data analysis algorithm can identify whether an insured member has been diagnosed with a specific rare genetic disease. For example, the insurance company device 140 executing the data analysis algorithm can search for the ICD10 code associated with a diagnosis of spinal muscular atrophy (SMA). Additionally or alternatively, the insurance company device 140 executing the data analysis algorithm can search for the NCD code associated with the drug Spinraza®, which is a drug used to treat SMA. Finding a prescription for Spinraza® can also indicates a diagnosis of SMA, which indicates that the person is ineligible for the rare gene insurance product.

In addition, the insurance company device 140 executing the data analysis algorithm can parse rows of the database and search claims data for the ICD10 code associated with Leber's congenital amaurosis or a combination of claims data that indicates the possibility of Leber's congenital amaurosis, such as being seen by a specialty eye doctor, claims related to a specific retinal scan, or being seen by a specialty clinician. A finding of any of these criteria can demonstrate a diagnosis or likely diagnosis in the future of Leber's congenital amaurosis, which indicates that the person is ineligible for the rare gene insurance product.

However, if the data analysis algorithm further identifies that an insured member has been treated through taking one of the rare gene therapy drugs (e.g. Zolgensma® for SMA or Luxturna® for Leber's congenital amaurosis), then the data analysis algorithm can identify that the insured member has been treated and cured of the disease and is therefore eligible for the rare gene insurance product.

In another embodiment, the data analysis algorithm can determine eligibility by analyzing insured member birth date. For example, the data analysis algorithm 504 can identify whether an insured member was born after an insured client began offering the rare gene insurance product or after an insured member enrolled his family in the rare gene insurance product. This method functions well for Zolgensma because Zolgensma only works as a curative therapy if taken by an infant under 2-years of age. In this embodiment, the data analysis algorithm can automatically enroll newly born insured members. In an alternative embodiment, the data analysis algorithm 504 can cover rare gene drug therapy insurance claims for insured members born after an insured member or an insured member's parents began enrollment of the rare gene insurance product.

In yet another embodiment the data analysis algorithm can determine eligibility by analyzing insured member employment start date. For example, the data analysis algorithm 504 can identify whether an insured member was diagnosed with a rare genetic disease after an insured member began employment with an insured client or if an insured member hired an insured member diagnosed with a rare genetic disease after enrolling all insured members associated with the insured client. In this embodiment, the data analysis algorithm can automatically enroll new hires to an insured member and can cover insurance claims for a rare genetic disease drug therapy for anyone hired after the date that the insured client enrolled its employees in the rare gene insurance product. Alternatively, any existing employees already diagnosed a rare genetic disease at the time that the insured client began offering the rare gene insurance product (i.e. hired before the insurance product start date) may not be eligible for the rare gene insurance product, and the insurance company may not cover any claims for the rare gene drug therapy for those existing, already diagnosed employees.

Further still, the data analysis algorithm can analyze additional information outside the data stored in the insurance storage device 142. For example, the insurance company device 140 executing the data analysis algorithm can search social media websites (e.g. Facebook) using the names stored in the insurance storage device 142. For example, the insurance company device 140 executing the data analysis algorithm can identify whether a social media account associated with an insured member's name is associated with any SMA or Leber's congenital amaurosis affinity groups (e.g. support groups, etc.). A finding that the social media account is associated with one of these affinity groups can indicate that the person is ineligible for the rare gene insurance product.

In some embodiments, the insurance company device 140 executing the data analysis algorithm can analyze data related to a subset of the insurance storage device 142, such as all the insured members (e.g. employees) associated with an insured client (e.g. a company of the employees).

Whether the data analysis algorithm 502 uses any of the above eligibility determination methods can be implemented on a drug-by-drug basis. For example, Zolgensma may use the birthdate method or the medical code method, while Roctavian may use the employment start date method. As such, an employee may be eligible for coverage for one drug, but ineligible for another.

After analyzing some or all of the data in the insurance storage device 142, the insurance company device 140 executing the data analysis algorithm can automatically enroll eligible insured members in step 608. Alternatively, ineligible insured members are denied access to the rare gene insurance product in step 610. In some embodiments, a finding that one insured member associated with the insured client is ineligible results in all insured members associated with the insured client being ineligible. Alternatively, in some embodiments, a finding that one insured member associated with the insured client is ineligible results in only the ineligible insured member being ineligible with all other insured members of the insured client remaining eligible. Steps 608 and 610 can include communicating to the benefit manager device 102 a yes or no value for some or all insured members analyzed by the data analysis algorithm. For example, step 608 and 610 can provide a list of names, and any other necessary information (e.g. social security numbers, addresses, etc.), to the benefit manager device 102 so that the benefit manager device 102 can automatically enroll the eligible insured members in the rare gene insurance product. In some embodiments, ineligible insured member's information is not communicated to the benefit manager device 102. Instead, the insurance company device 140 can communicate non-identifying numbers for each enrolled member to the benefit manager device 102. For example, John Smith can be represented by a rare genetic disease insurance product account number (e.g. 1234-567) without names or other identifying information.

Alternatively, the insurance company can simply provide the number of members who qualify to the benefit manager device, but omit any identification information. In this embodiment, the insurance company can receive premiums from the insured members who are enrolled in the rare gene insurance product and provide the premiums to the PBM. Furthermore, any claims under the rare gene insurance product can be made through the insurance company and passed to the PBM. Only during claim adjudication will insured member identification information be provided to the PBM.

Figure 7:
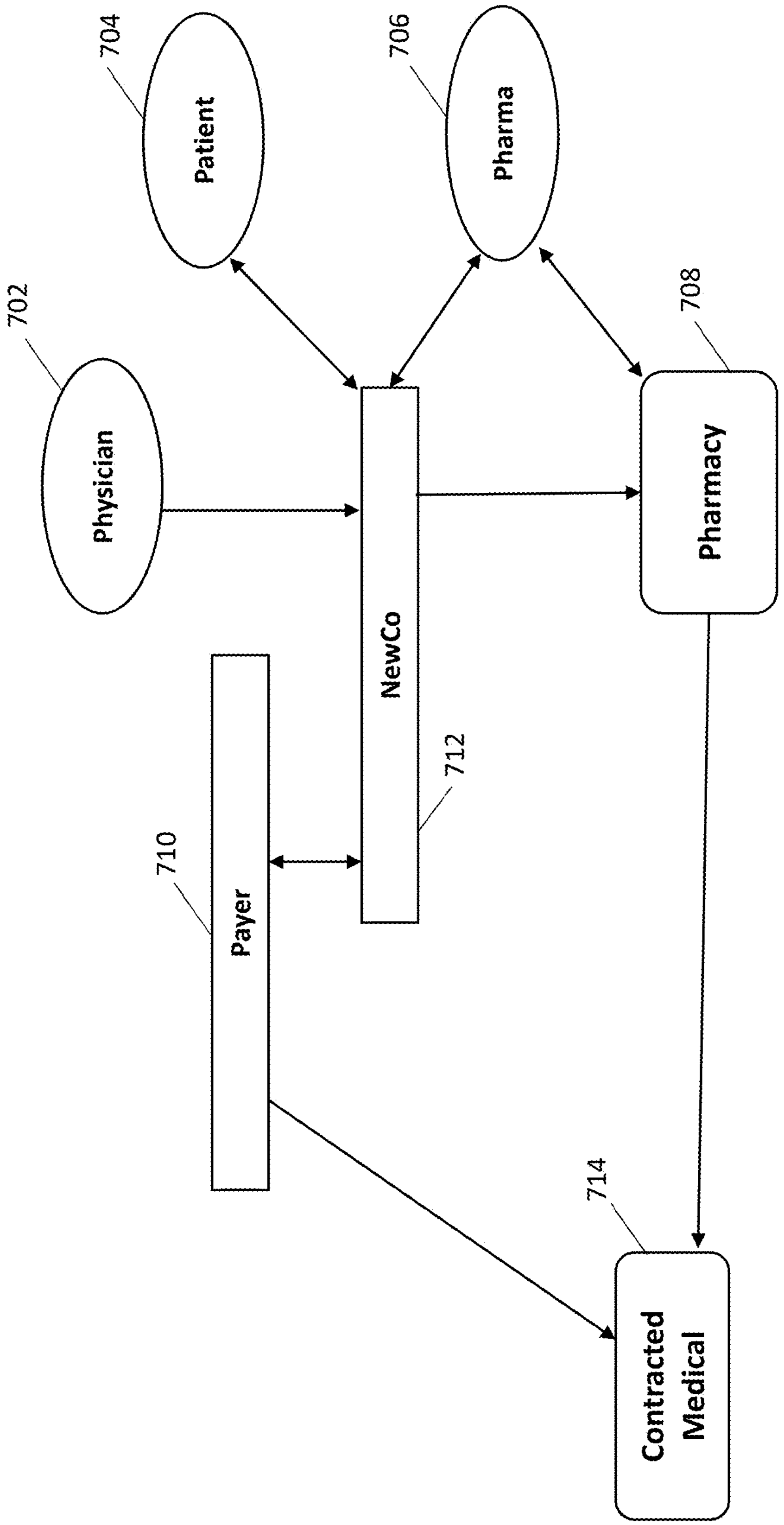
FIG. 7 is a block diagram of a flowchart illustrating capitated claim flows for the rare gene therapy insurance product, according to an example embodiment.
Figure 8:
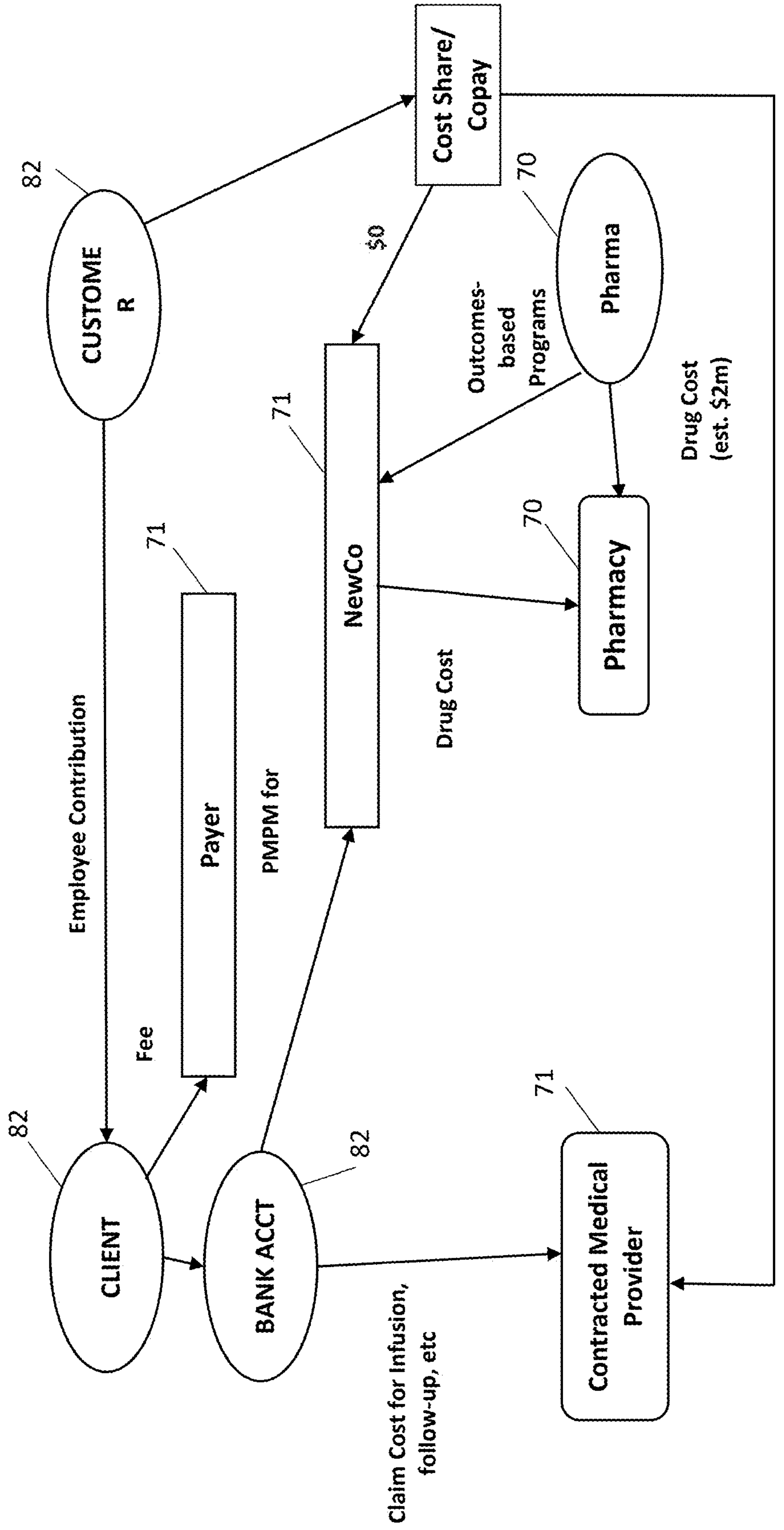
FIG. 8 is a block diagram of a flowchart illustrating capitated financial flows for the rare gene therapy insurance product, according to an example embodiment.

After an insured member has been enrolled in the rare drug insurance product, the insured member may submit a claim to pay for the rare gene therapy from the PBM or another entity offering the rare gene insurance product when diagnosed with a rare genetic disease which can be cured by a rare gene therapy. FIGS. 7 and 8 illustrate the claims and financial flow when a claim for one of the gene therapy drugs is made. As shown in FIG. 7, the claims data can include a physician 702 or patient 704 making a claim for the rare gene therapy drug to the entity offering the rare gene insurance product 712, the entity 712 submitting a claim to the payer 710, who authorizes the therapy. In addition, the entity offering the rare gene insurance product 712 requests the drug from a pharmacy 708, who receives the drug from a pharmaceutical company 706 providing the drug through the pharmacy 708 and providing the drug to be administered to a contracted medical provider 714, who then administers the drug to the patient 702.

Referring now to FIG. 8, the payment for the expensive gene therapies is illustrated. Via a cost share or co-pay method, which a customer 820 pays periodically, money is provided to the entity offering the rare gene insurance product 712. Also, a client who subscribes to the rare gene insurance product puts money in a bank account 822, and the bank account 822 pays money to the entity offering the rare gene insurance product 712 on a periodic basis. Also, the bank account 822 provides money to a contracted medical provider 714 whenever a medical treatment is provided. Also, the entity offering the rare gene insurance product 712 provides money to a pharmacy 708 whenever a prescription is fulfilled from a pharmaceutical company 706. Furthermore, repayment can include a co-pay from the customer 820, a payment from a client 824, and further payment from the insurance payer. Also, the pharmacy 708 and the pharmaceutical company 706 are paid for the drug. In some embodiments, the pharmaceutical company 706 is not paid if the drug does not cure the patient.

In this manner, the data analysis algorithm 502 can be handed over from one entity to another without sharing any information between the two entities. Only after a determination that a member should be automatically enrolled in the rare gene insurance product is made, can any private information pass between entities.

Furthermore, because the data analysis algorithm 502 can identify a database's organizational structure, the data analysis algorithm 502 can analyze data on any database without any prior knowledge about the database. Indeed, receiving prior knowledge about the database could subject the database to a data breach, thereby violating HIPAA or other data privacy laws.

Finally, despite analyzing sensitive data in another entity's database, the benefit manager device 102 does not learn anything about the sensitive information except when necessary. Therefore, insured members from many insurance companies can enroll in the rare gene insurance product without the sharing of sensitive information across entities (e.g. from insurance company to PBM). In addition, the benefit manager device 102 can run the data analysis algorithm 502 on its own data to enroll members of the PBM. Through these processes, a large pool of insured members can be built, thereby mitigating the risk associated with paying for such high-priced pharmaceutical drugs, such as Luxturna® and Zolgensma®.

As discovered by the present inventors, some organizations may be unwilling or unable to allow data analytics of organization-controlled databases to be performed by a third-party organization. For example, in the medical field, organizations are mandated by law (e.g. HIPAA) to protect their patient's medical data and make sure their patient's medical data is not shared. Therefore, a first company cannot analyze a second company's database without the second company being in violation of HIPAA despite the benefits such analysis across companies could provide. As such, there is a need in the art to develop data analyzers that do not share private information across organizations while still gaining insight from analyzing multiple databases. The present disclosure describes various embodiments for providing access and analysis of multiple databases and while maintaining data security, e.g., that required by law or for other sensitive business reasons.

Figure 9:
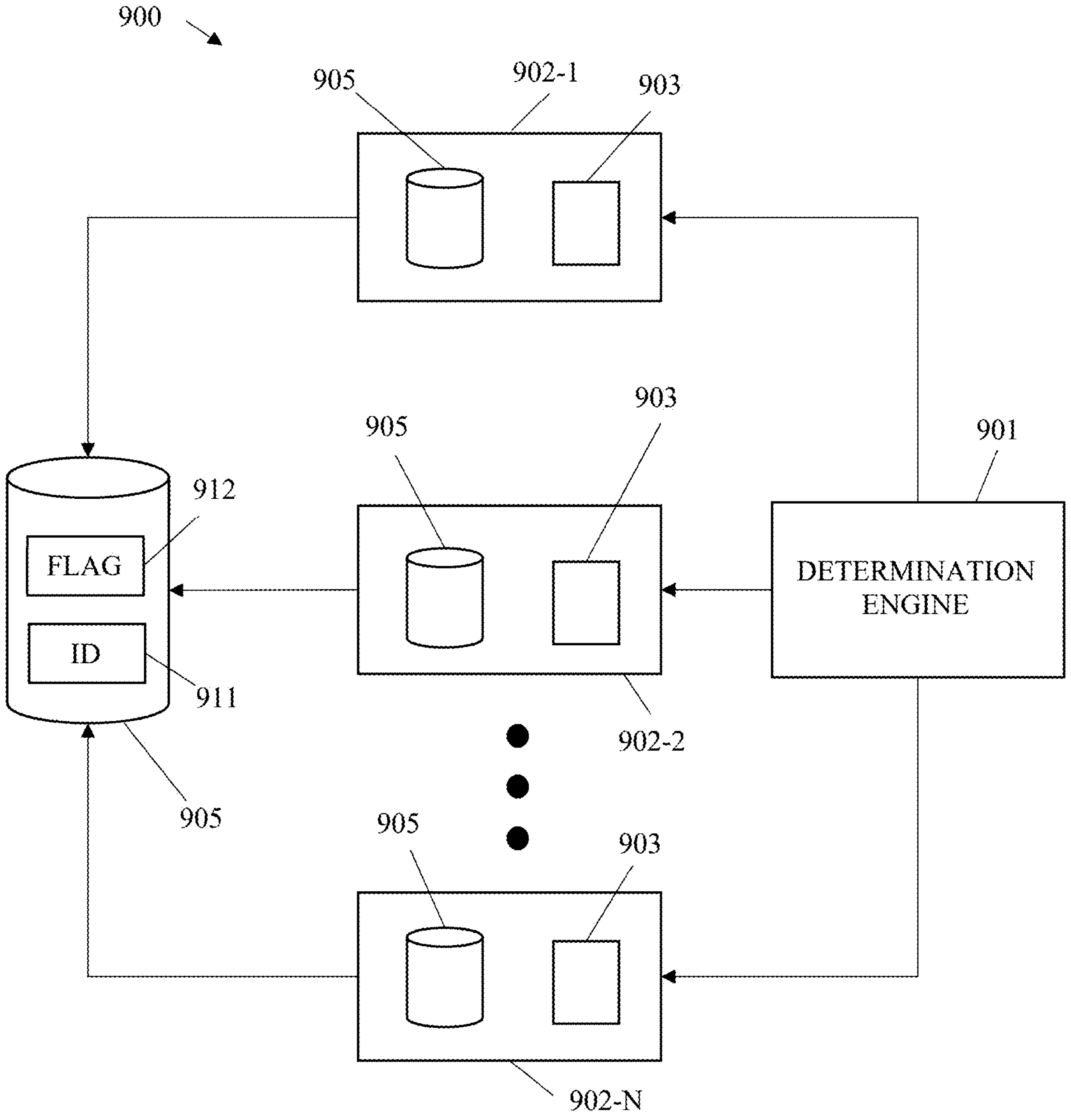
FIG. 9 is a schematic view of a computing system according to an example embodiment.

FIG. 9 shows a system 900 for analyzing multiple databases in parallel without first combining the databases while allowing restricted information to remain the respective electronic systems 902-1, 902-2, . . . 902-N. Monitoring and analysis across a plurality of databases can be more involved than monitoring a single database. Such parallelism commonly introduces additional complexities in performing database analysis and providing valid results. Here, the determination engine 901 has the algorithm for executing the analysis. The determination engine sends the algorithm to each electronic systems 902-1, 902-2, . . . 902-N. The electronic systems 902-1, 902-2, . . . 902-N include their own engines 903 (which include processors and local memory operable connected to the processor) that adapt the algorithm to operate on the individual database 905 within the electronic systems. Thus, each individual database 905 is analyzed by a same algorithm individually.

The determination engine 901 can set rules for the frequency of analysis or the individual databases 905. The determination engine 901 can set a rule to execute the algorithm on each individual database at a set time, e.g., daily, weekly, monthly, quarterly. In an example embodiment, the determination engine 901 can set the execution rule to be whenever a new member record is created in an individual database 905. In an example embodiment, approval into the global, covered database 904 of representations of member records can occur upon execution of the algorithm when a member record changes in a data field that is part of the algorithm. In an example embodiment, the algorithm looks for a new member record and the age of the member. If the member record includes an age field that indicates is outside the age range, the member record is excluded from the approved database 904. If the age field is inside the age range, the member record is included into the approved database 904. The approved member record is flagged and an identification code is generated and sent to the database 904 for tracking the covered member records on a global basis.

The determine engine 901 can update it algorithm to include multiple coverages for multiple scenarios. In the case of medical insurance for treatments that must be spread across multiple databases, the determination engine 901 can update the algorithm for the additional medical treatment, and the updated algorithm is sent for execution on each of the individual electronic systems 902 after any adjustments to the algorithm to comply with requirements of the individual database 905. The determination engine 901 can also produce a predicted result using the output from similar algorithms that were previously applied to the individual data bases. That is, the determination applies machine learning to compare prior algorithms with a new algorithm to predict the outcome when the new algorithm is applied to the individual databases. The predicted result can be the number of member records that will meet the requirements of the new algorithm to be part of the identified subset of records flagged to be identified in the resulting database 904.

The combined database 904 can store the representative records of the member records that qualify under the algorithm that is run on the individual electronic systems 902. The representative records are not copies of the member records from the individual electronic systems 902, which contain data that cannot be shared outside of the individual database locations. The representative records can include an identification field 911, which is representative of each member record in the individual electronic systems 902, and a flag field 912 that is associated with each representative identification field 911. The identification field 911 is stripped of all regulated or restricted information. In an example embodiment, the identification field 911 includes a code that is linked to a specific member record. The map of the identification field to the member record in the individual database 905 is stored back at the individual database 905. In an example embodiment, there is no information in the representative field that can tie back to a member record or identify an individual in the databases 905. The combined database 904 can be used for aggregation and identifying the number of individuals in the combined pool. The flag 904 can indicate if a particular representative record has been determined to be in pool by a positive flag value in the flag field 912 and outside of the pool by a negative value in the flag field.

The present system provides two views of the member records in the pool, namely an individual view at each of the individual databases 905 and an aggregated view at the combined database 904.

It is to be understood that other embodiments may be utilized and structural changes may be made without departing from the scope of the present disclosure, e.g., the parallel database analysis environment 900 or each of the individual databases 905 are further broken down in sub-databases that aggregate the member records and then send to the combined database 904.

In operation, a processor in the electronic systems 902 is configured to communicate with the individual database 905, analyze records stored in the database 905 using machine learning from the determination engine to identify a database organizational format of a database 905. The determination engine 901 receives a location, identify one or more locations for a set of member records (e.g., data) stored on the database 905 based on determining the organizational format of databases 905. The determination engine 901 searches, parses the set of data to identify whether any fields in the member records (e.g., entries) in the databases 905 associated with the set of data include a particular value that meets a decision criterion. The electronic systems 902 communicate over a network at least some of a first number of representative records of the member records identified in the database 905. The determination engine 901 further determines whether some records include the particular value. In an example embodiment, determination engine 901 further determines a first number of member records that include the particular value (and these can be flagged as positive) and a second number of member records in the database 905 that do not include the particular value (and these can be flagged as negative).

In an example embodiment, the particular value is a predetermined medical diagnosis code, a predetermined medical treatment code, or a predetermined prescription drug name. The particular value can also be an enrollment date or member age. The particular value can be combinations of these values stored in a member records.

In an example embodiment, the member records in the databases 905 include fields that are rows in a database. The one or more locations for the set of data stored on the database 905 includes at least a column of data in the database.

In an example embodiment, the determination engine 901 is further configured to identify the column of data in the member record in the database 905 storing the predetermined medical diagnosis code, the predetermined medical treatment code, or the predetermined prescription drug name to identify the database organizational format and the one or more locations for the set of data.

In an example embodiment, the determination engine 901 is further configured to determine that a first entry in a member record in a database 905 is ineligible for a benefit when the first entry is associated with the particular value. The determination engine 901 can automatically enroll a second entry in the benefit when the second entry is not associated with the particular value.

In an example embodiment, the determination engine 901 includes an algorithm to execute at least part of a benefit for a rare genetic disease insurance product that pays for a curative drug treatment for a rare genetic disease.

In an example embodiment, the determination engine 901 includes an algorithm to analyze each member record to determine if the member record is for an insured member having an insurance policy, and to automatically enroll the insured member when the second entry does not include the predetermined medical diagnosis code, the predetermined medical treatment code, or the predetermined prescription drug name indicating that the insured member has not been diagnosed with a rare genetic disease.

In an example embodiment, the determination engine 901 includes an algorithm or processor configured to render ineligible the insured member when the entry includes the predetermined medical diagnosis code, the predetermined medical treatment code, or the predetermined prescription drug name indicating that the insured member has been diagnosed with a rare genetic disease.

In an example embodiment, the determination engine 901 includes an algorithm to execute a machine learning process for linear discriminant analysis, maximum entropy classifiers, logistic regression, Naïve Bayes classifiers, or a neural network.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A. The term subset does not necessarily require a proper subset. In other words, a first subset of a first set may be coextensive with (equal to) the first set.

In this application, including the definitions below, the term "module" or the term "controller" may be replaced with the term "circuit." The term "module" may refer to, be part of, or include processor hardware (shared, dedicated, or group) that executes code and memory hardware (shared, dedicated, or group) that stores code executed by the processor hardware.

The module may include one or more interface circuits. In some examples, the interface circuit(s) may implement wired or wireless interfaces that connect to a local area network (LAN) or a wireless personal area network (WPAN). Examples of a LAN are Institute of Electrical and Electronics Engineers (IEEE) Standard 802.11-2016 (also known as the WIFI wireless networking standard) and IEEE Standard 802.3-2015 (also known as the ETHERNET wired networking standard). Examples of a WPAN are the BLUETOOTH wireless networking standard from the Bluetooth Special Interest Group and IEEE Standard 802.15.4.

The module may communicate with other modules using the interface circuit(s). Although the module may be depicted in the present disclosure as logically communicating directly with other modules, in various implementations the module may actually communicate via a communications system. The communications system includes physical and/or virtual networking equipment such as hubs, switches, routers, and gateways. In some implementations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various implementations, the functionality of the module may be distributed among multiple modules that are connected via the communications system. For example, multiple modules may implement the same functionality distributed by a load balancing system. In a further example, the functionality of the module may be split between a server (also known as remote, or cloud) module and a client (or, user) module.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of a non-transitory computer-readable medium are nonvolatile memory devices (such as a flash memory device, an erasable programmable read-only memory device, or a mask read-only memory device), volatile memory devices (such as a static random access memory device or a dynamic random access memory device), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, Javascript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

What is claimed is:

1. A rare disease system comprising:

a master database; and a master processor configured to communicate with the database and to load a local analysis program to multiple computing systems, with the local analysis program being based on machine learning to identify a database organizational format, identify one or more locations for a set of data stored on a local database based on the database organizational format, parse the set of data to identify whether any entries in the database associated with the set of data include a particular value, compare the particular value to a second value for each entry, and communicate over a network at least a first number of entries in the local database that are eligible for a benefit based on the comparison;

a plurality of local databases storing medical data in the set of data including genetic disease data, with at least one local database of the plurality of local databases being distinct from a second local database of the plurality of local databases;

a plurality of local processors operationally connected to the plurality of local databases and configured to execute the local analysis program on associated one of the plurality of local databases and return results to the master processor;

the master processor is further configured to:

determine that a first return result is ineligible for the benefit when the second value of the first entry is equal to the particular value, and automatically enroll a second return result for the benefit when the second value of the second entry is different from the particular value, and wherein the benefit is a rare disease insurance product that pays for a curative drug treatment for a rare disease.

2. The system of claim 1 wherein the particular value is at least one of a medical diagnosis code, a medical treatment code, a prescription drug name, or a combination thereof.

3. The system of claim 2 wherein the entries are rows in the plurality of local databases, and the one or more locations for the set of data stored on the plurality of local databases comprises at least a column of data in the database.

4. The system of claim 3 wherein the local processor is further configured to identify the column of data storing the medical diagnosis code, the medical treatment code, or the prescription drug name to identify the database organizational format and the one or more locations for the set of data.

5. The system of claim 4 wherein each entry is an insured member having an insurance policy, and wherein the master processor is configured to automatically enroll the insured member when the second value of the second return result does not include the medical diagnosis code, the medical treatment code, or the prescription drug name indicating that the insured member has not been diagnosed with a rare disease.

6. The system of claim 5, wherein the local processor is configured to flag ineligible an insured member record when an entry includes the medical diagnosis code, the medical treatment code, or the prescription drug name indicating that the insured member has been diagnosed with a rare genetic disease.

7. The system of claim 1 wherein the machine learning comprises linear discriminant analysis, maximum entropy classifiers, logistic regression, Naïve Bayes classifiers, a neural network, or a combination thereof.

8. The system of claim 7, wherein the master processor is further configured to train the machine learning using at least one of an SQL database format, a relational database format, a column-oriented database format, an operational database format, a key-value database format, a MySQL format, a DB2 format, a Microsoft SQL Server format, a NoSQL format, or a combination thereof.

9. The system of claim 1, wherein the master processor is further configured to pool outputs from the local analysis program running on distinct ones of the local databases to cover a rare disease over multiple populations stared in the distinct ones of the local databases.

10. The system of claim 9, further comprising controlling a pharmacy to dispense a rare disease drug related to the rare disease.

11. A rare disease processing method, comprising:

training a local analysis system using a master processor configured to communicate with a master database load a local analysis program to multiple computing systems using machine learning to identify a database organizational format, the local analysis program including instructions to identify one or more locations for a set of data stored on a local database based on the database organizational format, parse the set of data to identify whether any entries in the database associated with the set of data include a particular value, compare the particular value to a second value for each entry, and communicate over a network at least a first number of entries in the local database that are eligible for a benefit based on the comparison;

loading the local analysis program to multiple computing systems;

executing the local analysis program individually at a plurality of the multiple computing systems on a plurality of local databases storing medical data in the set of data including rare disease data, with at least one local database of the plurality of local databases being distinct from a second local database of the plurality of local databases;

returning output from the local analysis program on associated one of the plurality of local databases and return results to the master processor;

determining that a first return result is ineligible for the benefit when the second value of the first entry is equal to the particular value; and automatically enrolling a second return result for the benefit when the second value of the second entry is different from the particular value, and wherein the benefit is a rare disease insurance product that pays for a curative drug treatment for a rare disease.

12. The method of claim 11, wherein executing the local analysis program includes analyzing the local database with the particular value being at least one of a medical diagnosis code, a medical treatment code, a prescription drug name, or a combination thereof.

13. The method of claim 12, wherein executing the local analysis program includes analyzing rows in the plurality of local databases for the entries, and the one or more locations for the set of data stored on the plurality of local databases comprises at least a column of data in the database.

14. The method of claim 13, wherein executing the local analysis program includes identifying the column of data storing the medical diagnosis code, the medical treatment code, or the prescription drug name to identify the database organizational format and the one or more locations for the set of data.

15. The method of claim 11, wherein each entry is an insured member having an insurance policy, and wherein executing the local analysis program includes automatically enrolling the insured member when the second value of the second return result does not include the medical diagnosis code, the medical treatment code, or the prescription drug name indicating that the insured member has not been diagnosed with a rare disease.

16. The method of claim 11, wherein the executing the local analysis program further includes flagging as eligible an insured member record when an entry includes the medical diagnosis code, the medical treatment code, or the prescription drug name indicating that the insured member has been diagnosed with a rare genetic disease.

17. The method of claim 11, wherein training the local analysis program includes at least one of linear discriminant analysis, maximum entropy classifiers, logistic regression, Naïve Bayes classifiers, a neural network, or a combination thereof.

18. The method of claim 11, wherein training the local analysis program includes training the local analysis program using at least one of an SQL database format, a relational database format, a column-oriented database format, an operational database format, a key-value database format, a MySQL format, a DB2 format, a Microsoft SQL Server format, a NoSQL format, or a combination thereof.

19. The method of claim 11, further comprising pooling outputs from the local analysis program running on distinct ones of the local databases to cover a rare disease over multiple populations stared in the distinct ones of the local databases.

20. The method of claim 19, further comprising controlling a pharmacy to dispense a rare disease drug related to the rare disease.

* * * * *